US008483799B2

(12) United States Patent
Böing et al.

(10) Patent No.: US 8,483,799 B2
(45) Date of Patent: Jul. 9, 2013

(54) METHOD AND SYSTEM FOR COMPUTED TOMOGRAPHY ILLUSTRATION OF THE MOVEMENT OF A HEART

(75) Inventors: Dieter Böing, Erlangen (DE); Axel Kuettner, Tübingen (DE); Johann Uebler, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 1578 days.

(21) Appl. No.: 11/405,528

(22) Filed: Apr. 18, 2006

(65) Prior Publication Data

US 2006/0247518 A1 Nov. 2, 2006

(30) Foreign Application Priority Data

Apr. 19, 2005 (DE) .......................... 10 2005 018 066

(51) Int. Cl.
*A61B 5/05* (2006.01)
(52) U.S. Cl.
USPC ........... 600/424; 600/407; 600/437; 382/128; 382/132; 378/15; 378/901; 378/208
(58) Field of Classification Search
USPC .................. 600/407, 410, 437, 424; 382/128, 382/132; 378/15, 901, 208
See application file for complete search history.

(56) References Cited

U.S. PATENT DOCUMENTS

| 6,154,516 | A   | * | 11/2000 | Heuscher et al. ................ 378/15 |
| 7,289,841 | B2  | * | 10/2007 | Johnson et al. ................ 600/431 |
| 2003/0161435 | A1 |   | 8/2003 | Ozaki |
| 2004/0111025 | A1 | * | 6/2004 | Avniash et al. ................ 600/428 |

FOREIGN PATENT DOCUMENTS

WO WO 2004/037087 A2 5/2004

* cited by examiner

*Primary Examiner* — Unsu Jung
*Assistant Examiner* — Joel Lamprecht
(74) *Attorney, Agent, or Firm* — Harness, Dickey & Pierce

(57) ABSTRACT

A method and a system are disclosed for computed tomography illustration of the movement of a heart in the cardiac cycle with the aid of a spiral CT. In the method, a patient is administered a contrast medium via an electronically controllable apparatus. A stationary prescan of a cardiac artery is carried out in order to determine the sufficient filling of the artery with the automatically applied contrast medium. When a sufficient contrast medium filling is detected, the current heart rate of the heart being examined is measured, and a maximum possible feed rate for a spiral scan and a duration of the spiral scan are determined on the basis of the current heart rate. Subsequently, the spiral scan is carried out over the heart region with the maximum possible feed rate.

15 Claims, 3 Drawing Sheets

METHOD AND SYSTEM FOR COMPUTED TOMOGRAPHY ILLUSTRATION OF THE MOVEMENT OF A HEART

The present application hereby claims priority under 35 U.S.C. §119 on German patent application number DE 10 2005 018 066.3 filed Apr. 19, 2005, the entire contents of which is hereby incorporated herein by reference.

FIELD

The invention generally relates to a method and/or a system for computed tomography illustration. For example, it may relate to a method and/or system regarding the movement of a heart with the aid of a spiral CT, a 3D image series being produced over a cardiac cycle with the aid of a spiral scan.

BACKGROUND

Methods are generally known. A spiral scan is typically carried out over the heart region to produce an image series of the movement of a heart in the cardiac cycle, the heart being completely scanned over all cycle phases. Further, at least one cardiac cycle is used to reconstruct the cycle timing in a volume illustration.

An ECG is used as a rule to synchronize the recorded image data. It is also possible to determine the movement of the heart exclusively from the detector output data of the computed tomography, and thereby to assign the recorded detector data to the individual cardiac cycle phases and thus combine them to form a complete picture of the heart beyond a typical cardiac cycle. It is possible here to combine data originating from a number of cardiac cycles and, if appropriate, also from a number of X-ray tubes.

For the purpose of better recording and a high-contrast illustration of the cardiac vessels, a contrast medium is usually injected, that circulates in the blood circulation during the scan and provides a sufficiently high-contrast illustration.

A problem with such a cardio scan resides in the fact that, on the one hand, any avoidable radiation dose applied to the patient should be avoided. Even very slight radiation doses can cause lasting damage in the DNA of the cells that can possibly lead to an increased risk of cancer. On the other hand, as the contrast media used may have a damaging effect, the aim is to administer the smallest possible amount of contrast medium.

SUMMARY

It is an object of at least one embodiment of the invention to find a method and/or system for computed tomography illustration of the movement of a heart which, firstly, is attended by a reduced or even minimum radiation burden and, secondly, simultaneously also largely reduces the required amount of injected contrast medium.

If a patient is injected with a contrast medium in preparation for a cardio CT scan, this contrast medium injection produces a rise in heart rate that needs to be estimated and incorporated into the calculation of the maximum possible feed rate. However, there exists no unique, predictable relationship that would fix the definitive patient's heart rate as a function of the injected contrast medium concentration.

Since each patient reacts differently, in practice certain safety margins are factored in such that the entire CT scan does not lead to inadequate results owing to a defective coverage by the scan. Accordingly, at present a somewhat too low feed rate is currently used in practice for cardio scanning.

The inventors have realized, in at least one embodiment of the invention, that it is possible to enable a feed rate that is tuned much better to the actual conditions when the calculation of the feed rate actually used during the spiral scan is not performed until immediately before beginning the spiral scan and after the contrast medium injection has already been undertaken. In this case, the body has already reacted to the contrast medium present and has increased the pulse rate correspondingly, such that the pulse rate now measured corresponds substantially more accurately to the actual pulse rate during the cardio spiral scan then carried out. It is possible in this way to largely dispense with safety supplements. As such, the dose actually applied during the scan also corresponds only to the dose actually mandatory, and redundant scans do not take place.

In addition, there is now the possibility to calculate the actual scanning duration very accurately in advance, such that the contrast medium flow with which the contrast medium is injected into the patient's blood circulation can already be stopped before the actual spiral scanning of the heart is ended. That is to say, the actual subsequent course of the contrast medium between the injection point and the recorded cardiac arteries is taken into account such that a once again reduced amount of contrast medium need be applied overall.

In accordance with this, in at least one embodiment of the invention, the inventors propose an improved method for computed tomography illustration of the movement of a heart in the cardiac cycle with the aid of a spiral CT, having the following method steps:

a patient is administered a contrast medium via an electronically controllable apparatus for applying contrast medium, a stationary prescan of a cardiac artery, preferably the aorta, is carried out in order to determine the sufficient filling of the artery with the automatically applied contrast medium, as soon as a sufficient contrast medium filling is detected, the current heart rate of the heart being examined is measured, and the maximum possible feed rate for a spiral scan and the duration of the spiral scan are determined on the basis of this current heart rate, subsequently the spiral scan is carried out over the heart region with the maximum possible feed rate.

As a result of this novel method, the actual scanning time is reduced by up to approximately 10% in relation to the known situation, something which corresponds to a significant lowering of the radiation dose.

In accordance with a further embodiment of the inventive method, the inventors also propose that the contrast medium application is already stopped before the end of the spiral scan, the subsequent course of the contrast medium injection in the patient's blood circulation thereby being considered. Thus, in addition to the irradiation time that has already been reduced and leads in any case to a smaller amount of applied contrast medium, it is thereby also possible to additionally reduce contrast medium otherwise applied unnecessarily, the result also being a reduction in the damaging effect of the contrast medium in a significant fashion with reference to its effect.

According to an embodiment of the invention, use is made as maximum possible feed rate of the rate at which each point of the heart is detected during the spiral scan in relation to each cardiac cycle phase by altogether half a revolution of at least one X-ray tube. Thus, the feed rate is determined, in a fashion also seen, of course, in relation to the circumferential speed and to the width of the detector in the direction of the system axis, such that each point of the heart is scanned completely in each cardiac phase during the spiral scan, but redundant scans do not take place.

In an advantageous variant of an embodiment of the inventive method, sufficient contrast medium filling of a cardiac artery selected therefore can be detected during the prescan by a computer-aided image recognition method. For example, the image recognition method can automatically determine the contrast jumps present, the actual spiral scan being initiated automatically starting from a specific minimum contrast. In addition, there is also the possibility of intervening in the control of the contrast medium pump of the contrast medium applicator on the basis of this determined contrast and, if appropriate, of preventing a further increase in the contrast medium concentration in the patient's body.

The patient's heart rate can be determined, for example, by an ECG or by a pressure sensor at the patient's pulse. However, reference is explicitly made to the fact that although the detector output data can be assigned by using the measurement results obtained there it need not necessarily be used. There is also the possibility of assigning the detector output data to the corresponding cardiac cycle phases via the detector output data themselves.

In accordance with the embodiment of the method outlined above, the inventors further propose a system for computed tomography illustration of the movement of a heart, having the following system components:
- an arithmetic logic and control unit with data memories and program memories,
- a spiral computed tomography system with at least one X-ray tube for producing 3D image series of a beating heart,
- an apparatus for determining the heart rate,
- an electronically controllable apparatus for contrast medium application having a contrast medium pump,
- a first operating mode in which a stationary prescan of a cardiac artery, preferably the aorta, is carried out without feeding, in order to determine the sufficient filling of the artery with the automatically applied contrast medium, the current heart rate of the heart being examined being measured once the sufficient contrast medium filling has been reached,
- a program that determines the maximum possible feed rate for a spiral scan and the final instant of the spiral scan of the heart on the basis of this current heart rate, and
- a second operating mode in which a spiral scan of the heart is carried out with the maximum possible feed rate.

As already outlined, there is also the possibility here of providing a program or a program module that already stops the contrast medium flow before the end of the spiral scan such that, in addition to the radiation exposure, which is reduced in any case, it is also possible to reduce or even minimize the amount of contrast medium injected into the patient in a fashion that is overproportional relative to the reduced radiation burden.

It is further proposed that the system have a program for calculating the maximum possible feed rate which calculates the feed rate at which each point of the heart is detected during the spiral scan in relation to each cardiac cycle phase by altogether half a revolution of at least one X-ray tube. It is pointed out in this connection that when use is made of a number of, for example two, X-ray tubes to scan the heart the detector data that are obtained by the individual X-ray tubes offset in the direction of rotation can be combined such that, for example, quarter of a revolution of two X-ray tubes corresponds overall to half a revolution of one X-ray tube.

It is also possible in the case of an embodiment of the inventive system, to provide a program for detecting the sufficient contrast medium filling during the prescan which uses an image recognition method, in particular the detection of contrast jumps, to recognize the sufficient contrast medium filling and then, subsequently, to automatically initiate the actual spiral scan.

In accordance with an embodiment of the method outlined previously, in order to determine the heart rate the system can have an ECG or a pressure sensor at the patient's pulse by which the current heart rate can be detected at the beginning of the spiral scan and with the contrast medium already injected. The cycle phase for the cardio imaging need not necessarily, but can, be derived from this frequency measurement. Alternatively, a kymogram can be used for this purpose, for example.

BRIEF DESCRIPTION OF THE DRAWINGS

The invention is described in more detail below using an example embodiment with the aid of the figures, only the features required to understand the invention being illustrated, and the following reference symbols being used: 1: system for computed tomography illustration of the movement of a heart; 2: X-ray tube; 3: detector; 4: system axis; 5: ECG lead; 6: displaceable patient couch; 7: patient; 8: control line for the injector; 9: control and arithmetic logic unit; 10: control and data line to the CT; 11: injector; 12: contrast medium line; 21: start of the contrast medium injection; 22: prescan; 23: decision concerning sufficient contrast medium concentration in the heart; 24: measurement of the heart rate and calculation of the optimum feed rate and duration of the spiral scan; 25: start of the spiral scan; 26: premature switching off of the contrast medium flow; 27: end of the spiral scan; 28: reconstruction and output of the CT image sequences; 31: profile of the contrast medium flow; 32: concentration profile of the contrast medium in the heart; 33: threshold of the contrast medium optimum; I: first operating mode; II: second operating mode; C: contrast medium concentration; E: end of the spiral scan; S: start of the spiral scan; t: time; $\Phi$: concentration medium flow; $\Delta l$: lead time.

In detail.

DETAILED DESCRIPTION OF THE EXAMPLE EMBODIMENTS

Figure 1:
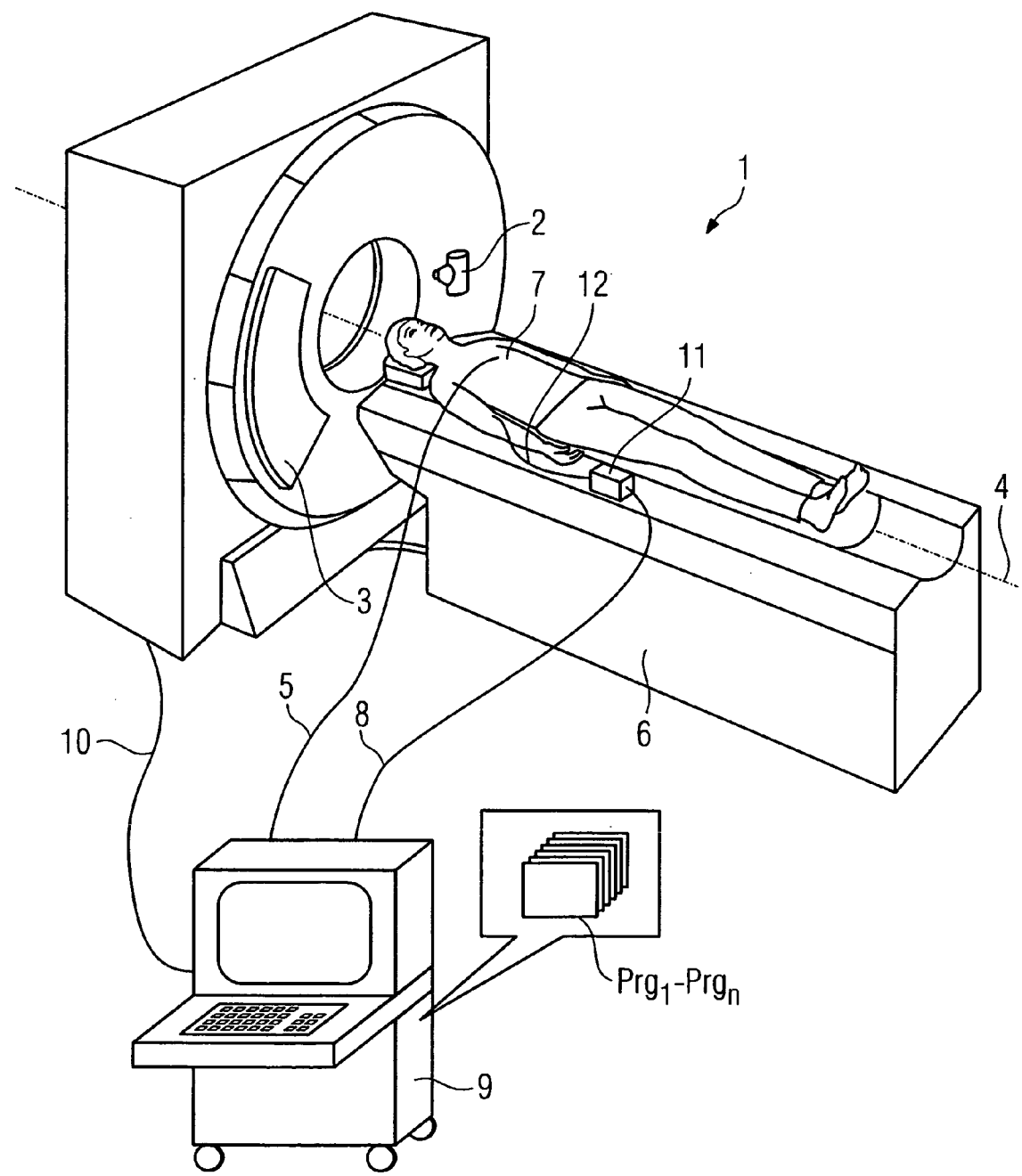
FIG. 1: shows an inventive system for carrying out a cardio spiral scan.

FIG. 1 shows an inventive system 1 including a control and arithmetic logic unit 9 in which there are present data memories with programs $Prg_1$-$Prg_n$, and the inventive control and data processing of the entire system is carried out. Of course, however, individual method steps and control tasks can also be distributed among different computers within the scope of the invention. The control and arithmetic logic unit 9 shown here is connected via a control and data line 10 to the actual CT, which has an X-ray tube 2 and, oppositely thereto, a detector that is fastened on a gantry and can move on a circular track in order to scan the patient.

During this scanning operation, a patient 7 who is located on a couch 6 that can be displaced in the direction of the system axis 4, is displaced in the direction of the system axis 4 such that, in the final analysis, spiral scanning takes place relative to the patient's coordinate system. The inventive system 1 additionally has an ECG that is integrated in the arithmetic logic unit 9 and scans the heart rate of the patient 7 via the ECG line 5. Furthermore, the control and arithmetic logic unit 9 uses the control line 8 to operate an injector 11 with the aid of an integrated contrast medium pump, and via the hose line 12 depicted this injector 11 injects the required contrast medium into the patient's 7 blood circulation at a prescribed flow rate.

According to at least one embodiment of the invention, the programs $Prg_1$ to $Prg_n$ stored in the arithmetic logic and control unit firstly push the patient 7 so far into the beam path of the CT that a so-called prescan of a cardiac artery can be carried out. There is no feeding of the patient 7 in the case of this prescan; rather, a tomogram of the heart is produced only in a plane of low dose rate in order to establish the contrast medium filling of an artery essential to the examination.

If the patient 7 is located in the correct prescan position, the injector 11 injects contrast medium at a prescribed flow rate, and either the operator uses the reconstructed tomogram output on a illustration screen to establish when there is a sufficient contrast medium filling in the observed cardiac artery, or an appropriate program can establish via automatic image processing whether sufficient contrast is present in the reconstructed image for a good illustration of the arteries. This mode of procedure corresponds to the first operating mode of an embodiment of the inventive system 1.

As soon as the system or operator establishes the presence of a sufficient contrast medium filling, the current heart rate of the patient 7 is measured, and this heart rate is used to determine the optimum feed rate. The points of the heart and the heart phases are scanned in relation to the rotational frequency of the gantry and the fan width of the beam path in a satisfactory, but not in redundant fashion in accordance with the desired time resolution of the images produced.

During the calculation of this optimum feed rate, the patient can already been displaced to the starting position for the following spiral scan. This corresponds to the second operating mode of an embodiment of the system 1. As such, the actual spiral scan can begin without delay after the correct feed rate is detected.

Since the temporal end of the scanning of the cardiac region is also simultaneously known, the contrast medium flow can now be turned off, in accordance with the runup known per se, between the contrast medium injection and the arrival of the contrast medium in the heart before the actual spiral scan has ended. This is possible because there is still sufficient contrast medium present in the patient's body for the remainder of the spiral scan owing to the coasting.

Owing to this optimized mode of procedure, on the one hand the exposure of the patient to radiation is reduced by up to approximately 10% by comparison with the conventional method. Further, at the same time, there is also an even more substantial reduction in the amount of the injected contrast medium in accordance with the shortened scanning time.

Figure 2:
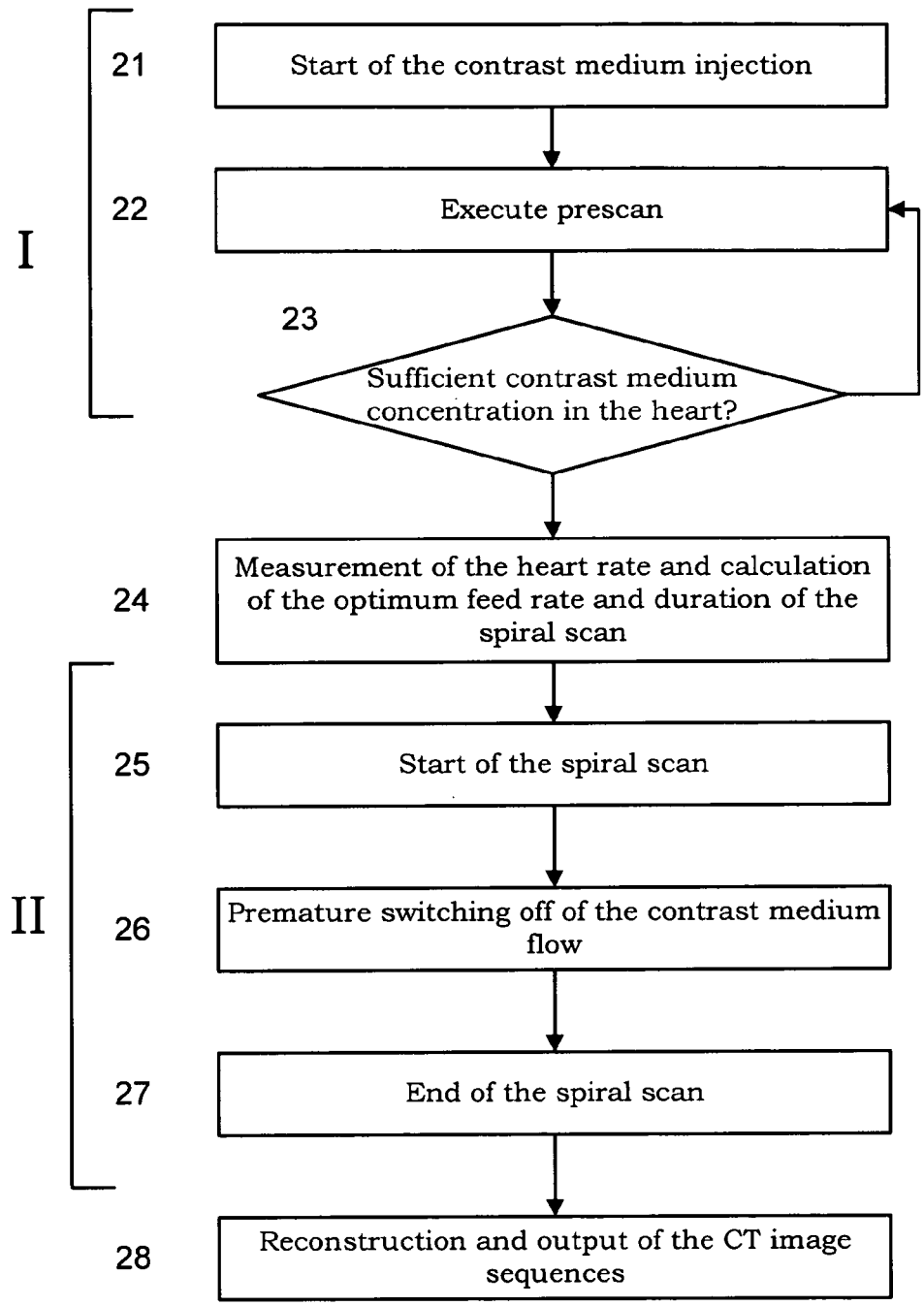
FIG. 2: shows a flow chart of an embodiment of the inventive method.

An embodiment of the inventive method cycle with the first operating mode I and the second operating mode II is illustrated once again schematically in FIG. 2. The contrast medium injection starts at 21 in the first operating mode I. Thereupon, the stationary prescan of the patient 22 is performed without feeding in order to determine the sufficient contrast medium filling of the cardiac arteries. The decision on this is taken at 23, the prescan 22 being continued in the case of an insufficient contrast medium concentration, while given a sufficient contrast medium concentration the first operating mode I is ended, and the current heart rate of the patient is measured at 24 under the influence of the contrast medium that is present, and the calculation is simultaneously determined for the optimum and fastest possible feed rate.

In this embodiment, the system now goes over into the second operating mode II by starting the spiral scan over the heart region at 25. In accordance with the precalculations and the already known end of the spiral scan, the contrast medium flow can be turned off prematurely at 26, and the end of the spiral scan is reached at 27. The second operating mode II of the system thereby ends. At 28, the computed tomography pictures are reconstructed using any desired, known reconstruction method, and the corresponding sequences can be output on a illustration screen.

Figure 3:
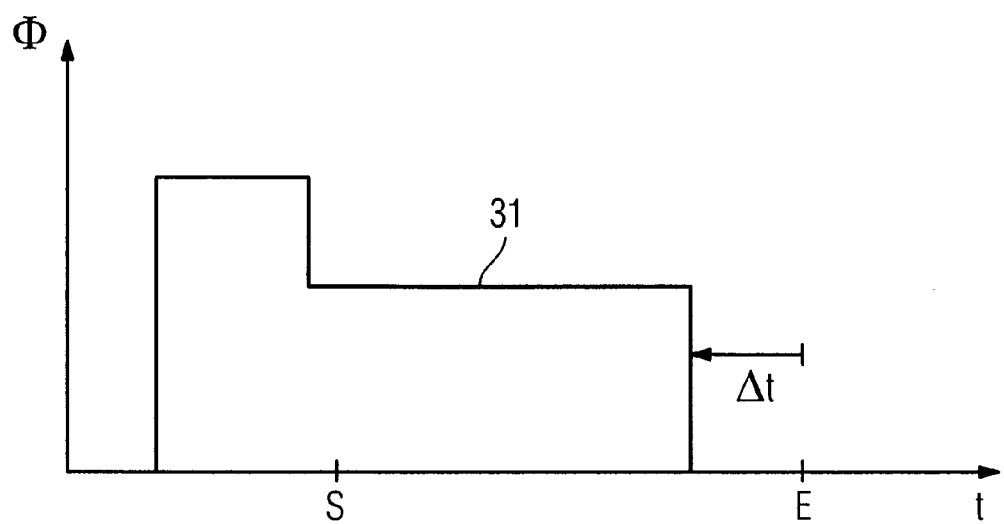
FIG. 3: shows a profile of the contrast medium flow at the injection site.
Figure 4:
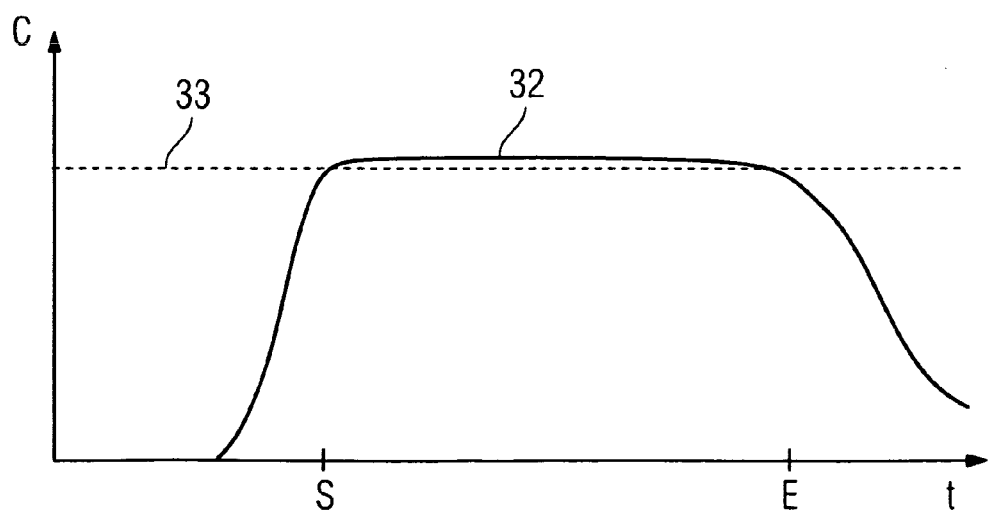
FIG. 4: shows the concentration profile of the contrast medium in a cardiac artery.

FIGS. 3 and 4 illustrate once more the background to the premature turning off of the contrast medium flow. FIG. 3 shows the profile 31 of the contrast medium flow $\Phi$, plotted against time t. It may be seen that the beginning of the injection starts with a relatively high flow rate. After a plateau has been reached in the circulation, the contrast medium flow can be reduced and can be kept largely constrast over the time of the actual spiral scan, which is marked at its start by S and at its end by E on the time axis.

The concentration profile 32 of the contrast medium concentration C in the heart is illustrated at the same time in FIG. 4 lying therebelow. A time delay is to be recognized between the beginning of the contrast medium injection and the rise in concentration in the heart until a plateau is reached. Once the optimum (indicated by dashes) in the contrast medium concentration 33, which leads to sufficient contrast in the imaging, is exceeded, the spiral scan begins with the start S and is continued up to the end E. Owing to the precise knowledge of the end of the spiral scan, it is possible—as illustrated in FIG. 3—for the contrast medium injection to be ended prematurely in accordance with the known lead time $\Delta t$ such that the drop in concentration of the contrast medium begins immediately after the end of the spiral scan.

It may be pointed out that the drop in concentration of the contrast medium shown in FIG. 4 is illustrated rather exaggeratedly and actually has a somewhat flatter profile.

It goes without saying that the above-named features of the invention can be used not only in the respectively specified combination, but also in other combinations or on their own without departing from the scope of the invention.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

What is claimed is:

1. A method for computed tomography illustration of a movement of a heart in a cardiac cycle with the aid of a spiral CT, the method comprising:
   providing a continuous infusion of a contrast medium to a patient using an electronically controllable apparatus;
   performing a stationary pre scan of a cardiac artery to determine a sufficient filling of the cardiac artery with the contrast medium, the sufficient filling being a minimum concentration of contrast medium in the cardiac artery such that the stationary prescan produces an illustration of the cardiac artery;
   measuring a current heart rate of the heart being examined immediately upon determining the sufficient filling of the cardiac artery with the contrast medium;
   determining a maximum possible feed rate for a spiral scan based on the current heart rate measured immediately upon determining that the cardiac artery has the sufficient filling of contrast medium that produces the illustration, the feed rate being a speed of a couch associated with the spiral CT;
   determining a duration of the spiral scan based upon the measured current heart rate; and
   subsequently performing the spiral scan over the heart region using the maximum possible feed rate such that at a start time of the spiral scan the cardiac artery has the sufficient filling of contrast medium;
   stopping the contrast medium administration before the end of the spiral scan such that the spiral scan continues after administration of the contrast medium to the patient ceases.

2. The method as claimed in claim 1, wherein the maximum possible feed rate is based on a rate at which each point of the heart is detected during the spiral scan in relation to each cardiac cycle phase associated with altogether half a revolution of at least one X-ray tube.

3. The method as claimed in claim 2, wherein the sufficient contrast medium filling is detected during the pre scan using computer-aided image recognition.

4. The method as claimed in claim 1, wherein the sufficient contrast medium filling is detected during the prescan using computer-aided image recognition.

5. The method as claimed in claim 1, wherein the current heart rate at the start of the spiral scan is determined by an ECG after the contrast medium has been injected.

6. The method as claimed in claim 1, wherein the current heart rate at the start of the spiral scan is determined by a pressure sensor configured to detect the patient's pulse after the contrast medium has been injected.

7. The method as claimed in claim 1, wherein the current heart rate at the start of the spiral scan is determined by an ECG after the contrast medium has been injected.

8. The method as claimed in claim 1, wherein the current heart rate at the start of the spiral scan is determined by a pressure sensor configured to detect the patient's pulse after the contrast medium has been injected.

9. A non-transitory computer readable medium including a data structure including program segments configured to implement the method of claim 1 when executed by a processor.

10. A system for computed tomography illustration of a movement heart, comprising:
   an arithmetic logic and control unit including one or more data memory and one or more program memory;
   a spiral computed tomography system including at least one X-ray tube configured to produce a n3D image series of a beating heart;
   an apparatus configured to determine a heart rate of the beating heart;
   an electronically controllable apparatus configured to continuously inject a contrast medium including a contrast medium pump, wherein
      a stationary prescan of a cardiac artery is performed in a first operating mode to determine a sufficient filling of the cardiac artery with an automatically injected contrast medium, the sufficient filling being a minimum concentration of contrast medium in the cardiac artery such that the stationary pre scan produces an illustration of the cardiac artery,
      the current heart rate of the heart being examined being measured immediately after the sufficient contrast medium filling has been reached,
      a program determines a maximum possible feed rate for a spiral scan based on the current heart rate measured immediately upon determining that the cardiac artery has the sufficient filling of contrast medium that produces the illustration, the feed rate being a speed of a couch associated with the spiral computed tomography system,
      the program determines a final instant of the spiral scan of the heart based on the current heart rate,
      a spiral scan of the heart is carried out in a second operating mode using the maximum possible feed rate such that at a start time of the spiral scan the cardiac artery has the sufficient filling of contrast medium, and
      the contrast medium flow is stopped before the end of the spiral scan such that the spiral scan continues after administration of the contrast medium to the patient ceases.

11. The system as claimed in claim 10, wherein the maximum possible feed rate is calculated based on the feed rate at which each point of the heart is detected during the spiral scan in relation to each cardiac cycle phase associated with half a revolution of at least one X-ray tube.

12. The system as claimed in claim 10, wherein the program is configured to detect the sufficient contrast medium filling during the prescan using image recognition.

13. The system as claimed in claim 10, wherein the apparatus configured to determine a heart rate is an ECG.

14. The system as claimed in claim 10, wherein the apparatus configured to determine a heart rate is a pressure sensor configured to detect the patient's pulse.

15. A system for computed tomography illustration of the moment of a heart, comprising:
   means for producing 3D image series of a beating heart;
   means for determining a heart rate of the beating heart;
   means for performing a stationary prescan of a cardiac artery to determine a sufficient filling of the cardiac artery with continuously infused contrast medium, the sufficient filling being a minimum concentration of contrast medium in the cardiac artery such that the stationary prescan produces an illustration of the cardiac artery, the current heart rate of the heart being examined being measured immediately upon determining the sufficient contrast medium filling has been reached;
   means for determining a maximum possible feed rate for a spiral scan based on the heart rate measured immediately upon determining that the cardiac artery has the sufficient filling of contrast medium that produces the illustration, the feed rate being a speed of a couch associated with the system for computed tomography;
means for determining a final instant of the spiral scan of the heart based on the heart rate; and
means for performing a spiral scan of the heart with the maximum possible feed rate such that at a start time of the spiral scan the cardiac artery has the sufficient filling of contrast medium;
means for stopping the continuous contrast medium infusion before the end of the spiral scan such that the spiral scan continues after administration of the contrast medium to the patient ceases.

* * * * *

UNITED STATES PATENT AND TRADEMARK OFFICE
CERTIFICATE OF CORRECTION

| | | |
|---|---|---|
| PATENT NO. | : 8,483,799 B2 | Page 1 of 1 |
| APPLICATION NO. | : 11/405528 | |
| DATED | : July 9, 2013 | |
| INVENTOR(S) | : Boing et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1709 days.

Signed and Sealed this
Sixth Day of January, 2015

Michelle K. Lee
*Deputy Director of the United States Patent and Trademark Office*